Figure 1:
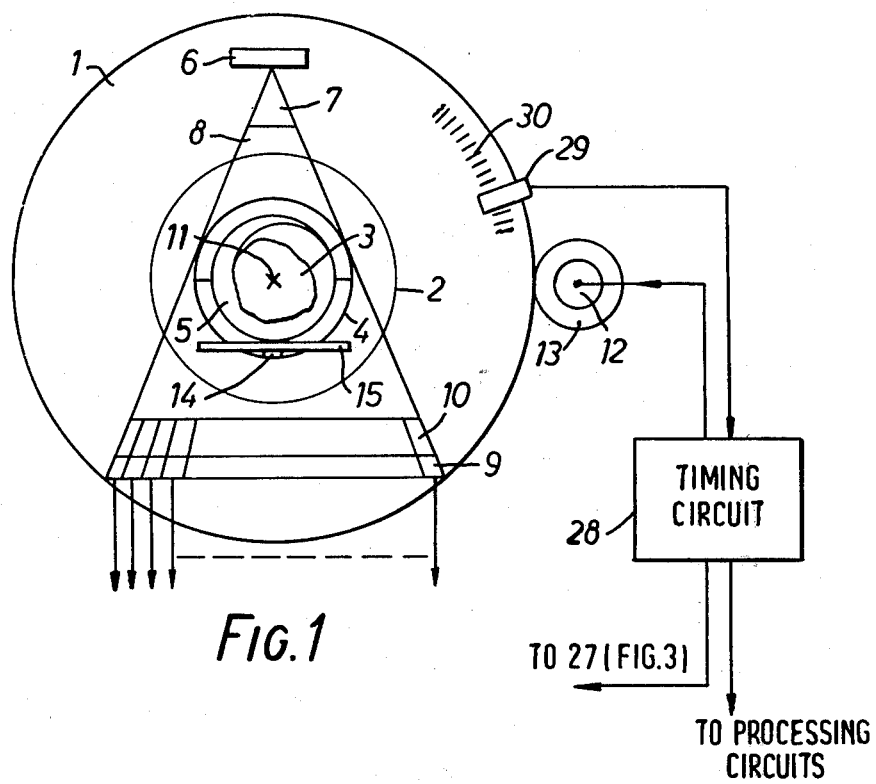

United States Patent [19]

Gibbons et al.

[11] 4,070,581

[45] Jan. 24, 1978

[54] DETECTION OF RADIATION

[75] Inventors: David John Gibbons, Uxbridge; Wieslaw Antoni Karwowski, Perivale; Charles Phillip Cousins, London, all of England; Ian MacDonald Green, Buckie, Scotland; John James Jarrett, Chalfont St. Peter, England

[73] Assignee: EMI Limited, Middlesex, England

[21] Appl. No.: 702,093

[22] Filed: July 2, 1976

[30] Foreign Application Priority Data

July 10, 1975 United Kingdom ............... 29010/75

[51] Int. Cl.² .......................................... G01M 23/00
[52] U.S. Cl. ............................................... 250/445 T
[58] Field of Search ................... 250/445 T, 366, 370

[56] References Cited

U.S. PATENT DOCUMENTS

| | | | |
|---|---|---|---|
| 3,890,506 | 6/1975 | Berninger | 250/370 |
| 3,936,638 | 2/1976 | Gibbons | 250/370 |
| 3,970,853 | 7/1976 | Kuhl et al. | 250/445 T |

Primary Examiner—Bruce C. Anderson
Attorney, Agent, or Firm—Cooper, Dunham, Clark, Griffin & Moran

[57] ABSTRACT

In a computerized axial tomographic apparatus it is proposed to use, as radiation detectors, alkali halide scintillator crystals cooperating with photodiodes to measure the light output therefrom, or else photodiodes directly sensitive to the radiation passed through the patient. For advantageous operation, especially in regard to drift and rapidity of operation, it is proposed to use the photodiodes photovoltaically and in the so-called "current mode".

11 Claims, 3 Drawing Figures

DETECTION OF RADIATION

The present invention relates to the detection of ionizing radiation, and it relates more particularly to the detection of such radiation on its simultaneous emergence from a body along a plurality of substantially co-planar and substantially linear beam paths; such detection being required, for example, in a computerized axial tomographic apparatus which produces a representation of the absorption (or transmission) coefficients at different locations distributed over at least one crossectional region of a body.

Computerised axial tomographic apparatus is described in U.S. Pat. No. 3,778,614, and since the demonstration of such apparatus the art of computerized axial tomography has developed rapidly. The early forms of such apparatus were most suitable for scanning the skull, because acquisition of the necessary data signals, i.e. signals indicative of the amount of radiation projected through the skull along each of a large number of substantially co-planar and substantially linear beam paths, took a substantial time (e.g. four minutes or more). Such a long acquisition time could not be tolerated in an apparatus for scanning the human torso, as movements of organs within the irradiated area would be almost certain to occur during the acquisition time, and this would result in blurring of the representation.

As it was clear that it would be beneficial to obtain in respect of the human torso, representations of the kind which it was possible to obtain in respect of the human skull, much effort has been expended in attempts to speed up the acquisition times of such apparatus.

The early apparatus for scanning the skull, the so-called brain scanner, used a source of a single beam of X-radiation and a single detector, mounted at the opposite side of the body to the source, for detecting the amount of radiation emergent from the body along the beam. The source and the detector were scanned laterally across the skull so that the beam assumed a number of parallel positions across the skull, and then rotated through a small angle, such as $\frac{1}{2}°$, about an axis, in the centre of the skull and perpendicular to the plane in which the lateral scanning took place. The lateral scan was then repeated in the opposite direction, to be followed by a second rotation and so-on, the alternate lateral and rotational movements being continued until the sum of all the rotational movements was 180°. It was realised that the sensitivity of the detector, which comprised a thallium activated sodium iodide crystal and an associated photomultiplier tube in optical communication therewith, could drift during the acquisition time, and that such drifting could cause the production of artefacts in the representation. It was found, however, that the scanning procedure described above tended to distribute errors evenly over the representation so that they did not mask true signals. In addition, the use of lateral scanning movements enabled the beam to be directed through reference attenuating media situated outside the region occupied by the skull. This permitted the detector sensitivity to be checked against a reference value after each lateral scan, and adjustments made as appropriate.

In order to make a computerized axial tomographic apparatus having an acquisition time sufficiently rapid to render it more suitable for examining the human torso, but without losing the aforementioned benefits of lateral scanning, the arrangement described in U.S. Pat. No. 3,946,234 was adopted and is used, for example, in the "EMI-Scanner" system Model 5005 supplied in the U.S.A. by EMI Medical, Inc. This technique involves the use of a source of a fan shaped of radiation and a plurality of detectors disposed to receive radiation travelling along respective beam paths in the spread; the paths of course being divergent as they travel from the source to the detectors. In the system referred to above, the angle of the fan is 10° and thirty detectors are used; the source and the detectors being scanned laterally across the body and rotated around it as before, except that the angular steps through which rotation is effected are commensurate with the fan angle 10°. This system is capable of completing the data acquisition in 20 seconds or less.

In order to effect a substantial further increase in the data acquisition rate of such apparatus, it has been proposed to dispense with the translational movement and to cause the source to provide a wider fan-shaped beam which substantially encompasses the body so that the data can be acquired by rotational movement of the source around the body. The translational movement may be retained, to a limited extent, if desired, by making use of an X-ray tube which has facilities for repetitively deflecting the electron beam of the tube across the anode thereof. The extent of such movement, however, is necessarily small (typically an inch or two) as compared with the extent of the lateral scan physically imparted to the source in the arrangement previously described. For this reason, the system of the general kind described in this paragraph, whether or not the deflected beam kind of X-ray tube discussed above is used, are referred to as "rotation only scanners", the significance being that the X-ray tube as a whole is subjected only to a rotational movement around the body and is not physically scanned laterally across the body.

In both kinds of rotation only scanner, the benefits of lateral scanning have, to at least some extent, been forfeited in the interests of rapid data acquisition. This means that the problem of drift may again become significant and, moreover, because a wide fan of radiation is used, many detectors — for example a hundred or more-are required and thus the problem of relative drifts in the sensitivities of different detectors may become important.

The thallium activated sodium iodide crystal and photomultiplier assembly which proved suitable for use as detector in translation type scanners, may be subject to too much drift for use in rotation only scanners. Other detectors have been tried, for example noble gas under pressure, but these, although substantially drift free, may be too slow in operation for rotation only scanners. It is an object of this invention to provide an arrangement for detecting ionising radiation which is substantially free of drift and which is rapid enough in operation for a rotation only scanner.

According to the invention there is provided in a rotation only scanner (as herein defined) for computerised axial tomography, an arrangement for detecting ionizing radiation simultaneously emergent from a body along a plurality of substantially co-planar beam paths comprising a detector element for each of said paths, each element including a semi-conductive device a *p-n* junction region operated in the photovolatic current mode as hereinafter defined. The semi-conductive devices may not themselves be directly exposed to the ionizing radiation but may be instead exposed to visible radiation derived from respective scintillator crystals which are exposed to the ionizing radiation. In other words, each detector element may comprise, so far as active compounds are concerned, a crystal and a semi-conductive device or merely a semi-conductive device.

It will thus be appreciated that the invention resides in the use, as radiation detectors in a rotation only scanner for computerized axial tomography, of photovoltaic current mode operated semi-conductor devices. The devices can either be directly exposed to the radiation or exposed to visible radiation generated in a scintillator in response to the incidence on said scintillator of the ionizing radiation. The use of a scintillator and a photo-diode to detect radiation is not claimed as being novel per se; it has been disclosed for example in "Photoeffects in Silicon Surface Barrier Diodes" Journal of Applied Physics, January 1962, p148—155, and in British Patent Specifications Nos. 1,121,986 and 827,977; the latter describing operation of an integrated X-ray detector in both the photovolataic and the photoconductive modes. None of these citations however, indicates that the use of photovoltaically operated semiconductive devices as detectors in a rotation only scanner for computerized axial tomography gives considerable advantages over other techniques especially as regard to drift and rapidity of operation. The arrangement of the invention also has advantages in that the weight and bulk of the detectors is low, and these are important considerations in rotation only scanners.

Furthermore, although the detectors per se have been known for a considerable time (i.e. at least since 1962) their use has not, so far as the applicants are aware, been proposed in computerized axial tomography, nor has it been indicated that such detectors might be useful for that purpose, despite the considerable commercial incentives to increase the data acquisition rate of such apparatus.

Figure 3:
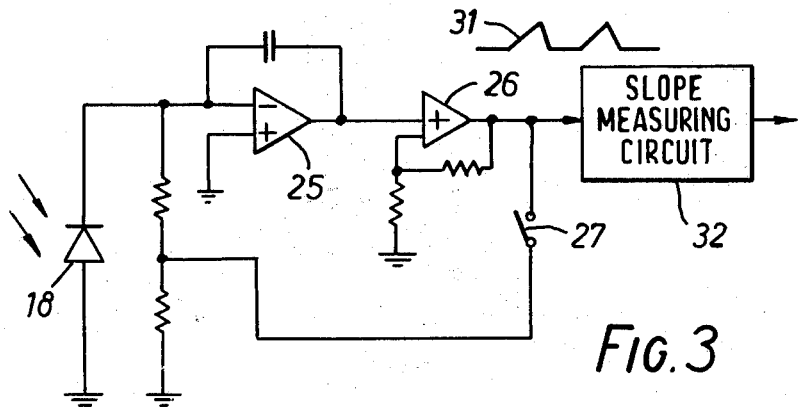
Figure 2:
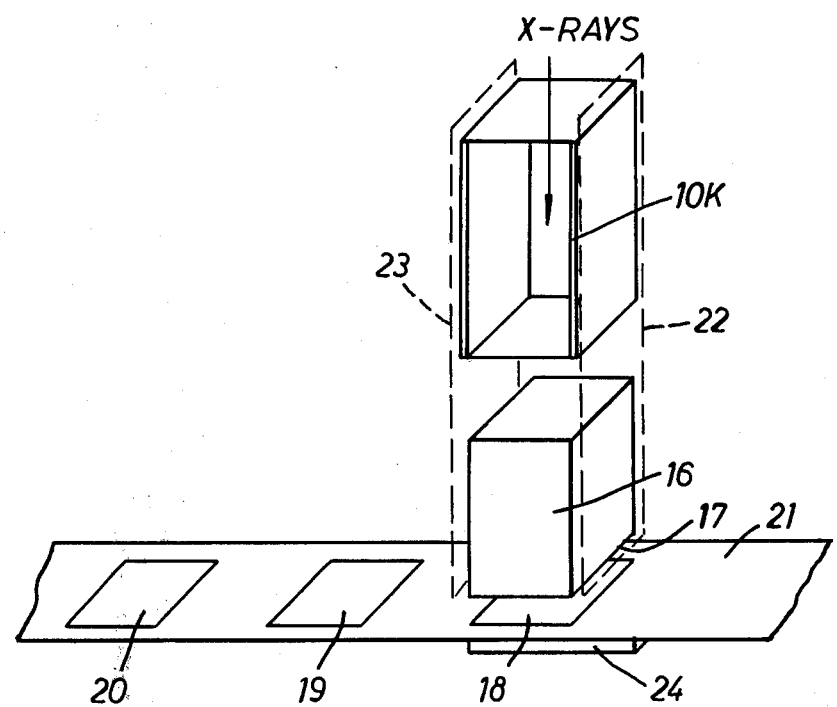

In order that the invention may be clearly understood and readily carried into effect, one embodiment thereof will now be described, by way of example only, with reference to the drawing, where:

FIG. 1 shows, in front elevation view, a rotation only scanner including an arrangement in accordance with one example of the invention, FIG. 2 shows, in perspective view, part of the arrangement incorporated in the scanner shown in FIG. 1, and FIG. 3 shows, in block schematic form, a diagram of a circuit for accepting and operating on output signals derived from a detector arrangement in accordance with the invention.

Referring now to FIG. 1, a turntable member 1 is formed with a central aperture 2, in which a body 3 to be examined is disposed within a two-part circular collar 4. Trapped between the collar 4 and the body 3 is a material 5, such as water in a flexible bag, which is provided in order to exclude air from the periphery of the body, at least to such an extent is practical.

The turntable member 1 carries a rotating anode X-ray tube 6, which constitutes a source of X-rays, and a collimator 7, associated therewith, which selects from the radiation emitted by the tube 6 a fan shaped swath 8 which is substantially planar, the plane of radiation being about 1cm. in thickness. The swath 8 of radiation is disposed, as shown in the drawing, so that it spans the collar 4. Disposed on the opposite side of the body 3 to the source tube 6, and also carried by the turntable member 1, is a detector arrangement 9, the construction of which will be more fully described hereinafter, and, interposed between the arrangement 9 and the body 3, a bank 10 of collimators.

The turntable member 1 and its attachments are rotatable about an axis 11 in the centre of the aperture 2 by means of a motor 12 which drives a gear wheel 13, the latter engaging with gear teeth (not shown) formed all around the outer periphery of the turntable member 1. The body is held stationary while the turntable member 1 rotates around it, and the body is also located so that the swath 8 irradiates a selected plane of the body. The location of the body 3 in relation to the turntable member 1 and its attachments is achieved by securing a flange 14, formed integrally with the collar 4, to a support member 15 upon which the rest of the body is supported supine. The support member 15 comprises two spaced parts, one in front of the member 1 and one behind it, the gap between the two parts being for the purpose of allowing the radiation to pass through it.

The detector arrangement 9 comprises a bank of scintillator crystals, each arranged to produce a light in response to the incidence thereon of ionizing radiation, and the light produced by each crystal is directed on to a respective photo-diode which produces an electrical output signal indicative of the amount of light incident thereon, which amount of light is, in turn, indicative of the amount or ionizing radiation incident on the corresponding scintillator crystal.

Although not shown in FIG. 1, it can be desirable in some circumstances to provide one or more shaped attenuators in the path of the ionizing radiation with the object of causing all of the detectors in the bank 9 to receive substantially equal amounts of radiation at a given time, despite the different thicknesses of the body disposed in the paths of different beams. The attenuator (or attenuators), if provided, is secured to the member 1 so that it rotates with the source and the detector devices, around the body.

Referring now to FIG. 2, part of the detector arrangement is shown in more detail. Ionizing radiation emergent from the body (not shown in FIG. 2) in a particular direction passes through a collimator $10_k$ of the collimator bank and is incident upon a scintillator crystal 16 which may be conveniently formed of thallium activated caesium iodide. The crystal 16 produces visible radiation the amount of which is indicative of the amount of ionizing radiation incident on the cystal, and the visible radiation so produced emerges through an output surface 17 of the crystal and falls upon a respective photo-diode 18 which provides an electrical output signal indicative of the amount of visible radiation incident thereon. In order to improve the efficiency of transfer of the visible radiation from the crystal 16 to the photo-diode 18, all surfaces of the crystal apart from the output surface 17 can be silvered. This can be conveniently achieved by means of a reflective film transparent to the X-rays, for example aluminium foil, secured in relation to the relevant faces of crystal but not in close contact thereto.

The photo-diode 18, together with a plurality of others, two of which are shown at 19 and 20 respectively, and each of which has an associated crystal such as 16 and collimator such as $10_k$, is formed upon a strip 21 of printed circuit board. The photo-diodes are all similar, and are suitable silicon p-n diodes which are operated in photovoltaic manner (i.e. with no externally applied voltage), and in the so-called current mode in which any voltage across the diode is kept as low as possible and at least significantly less than the diffusion voltage for the junction. The operation of the photo-diodes in photovoltaic current mode is of considerable importance, from the point of view of noise reduction, because the dark current and the noise current is less than for the same devices operated in other modes and in particular the more usual photo-conductive mode with externally applied reverse bias voltage. This improvement is obtained because the depletion region in the vicinity of the diode junction becomes wider as a voltage across the junction increases, thus increasing the capture region for thermally generated charge carriers.

Since, by operating the photo-diodes in the photovoltaic current mode, the depletion region is caused to be small so as to reduce their response to noise, correspondingly it is necessary to ensure that the charge carriers generated in response to the visible radiation from the crystals (i.e. the "wanted" charge carriers) are generated, so far as is possible, in the depletion region, otherwise the wanted carriers will not be collected and the efficiency of the photo-diodes will be reduced. In this example of the invention, it is arranged that the visible radiation is absorbed in the vicinity of the diode junction by constructing each diode so that the $p$-$n$ junction is near to the illuminated surface thereof, and typically less than the diffusion distance of the wanted carriers from that surface. This distance, D, is given by the formula:

$$D = (\Delta \tau)^{\frac{1}{2}},$$

where $\Delta$ is the diffusion constant of the wanted carriers in silicon and $\tau$ is the mean free lifetime of these carriers.

It has been found that good operation efficiency is achieved with a diffused planar $p$-$n$ junction between 0.1 and 1.0$\mu$m deep, with the visible radiation being incident upon the surface of the diode nearer the junction.

Reverting to the crystal 16, it has been found that, for the detection of X-rays of energy about 100kV, the crystal depth in the direction of incidence of the X-rays should be between 3mm and 5mm. The two other directions depend greatly upon the parameters involved in the investigation and the accuracy with which the resulting representation is to be produced, but typically the two dimensions of the surface crystal upon which the X-radiation is incident are 10mm and 2mm respectively.

Shields such as 22 and 23 are provided between adjacent crystals to reduce the possibility of the ionizing radiation passing from one crystal to an adjacent one, thus causing a phenomenon known as "cross-talk". The shields typically comprise foils of lead, tantalum or uranium, for example, or of alloys containing any of these materials.

It is convenient, when using the form of construction shown in FIG. 2, to provide circuits for receiving and operating on the electrical signals provided by the photo-diodes such as 18 in the form of hybrid films on the opposite side of strip 19 to the photo-diodes. One such circuit is shown schematically at 24, and such circuits are connected to other processing circuits which permit the output signals from all photo-diodes at many positions around the body to be correlated and processed in order to provide the desired representation.

As shown in FIG. 3, a circuit such as 24 can include an integrator 25 for integrating the output current from a photo-diode, which current may be between $10^{-13}$A and $10^{-9}$A. The integrated current is amplified by means of an amplifier 26 and the integrator is periodically discharged by means of an electronic switch, shown schematically at 27. This switch is operated under the control of a master timing circuit 28 (see FIG. 1) which also controls the scanning of the apparatus by way of motor 12, and which receives information concerning the progress of the scanning from a photocell/detector unit 29 (FIG. 1) which co-operates with a graticule 30 (FIG. 1) formed on the turntable member 1. Referring again, to FIG. 3, the output signal derived from the amplifier 26 is a sawtooth waveform 31. The slope of waveform 31 in any integration period is proportional to the mean photodiode current during that period and thus the waveform 31 is applied to a convenient slope measuring circuit 32. Preferably the circuit 32 is of the form described in U.S. Application Ser. No. 682,159 filed Apr. 30, 1976, which produces output pulses of length directly proportional to the mean photo-diode current.

The input stage of the integrator 25 must exhibit a high input impedance, and must also exhibit low offset voltage and current. If this is not the case, the photovoltaic action of the photo-diodes will be impaired, giving rise to unwanted dark currents.

The output signals from the circuits 32 can be processed in any convenient manner, such as that described in the aforementioned Patent Specification or that described in U.S. Pat. No. 3,924,129.

Although the embodiment of the invention just described is one in which a diode is exposed to visible radiation, in another embodiment the ionizing radiation is allowed to fall directly on a suitable diode. In that case, however, it is preferable for the ionizing radiation to enter the diode in such a direction that it travels along, rather than through, the diode junction. This enables a substantial number of the "wanted" carriers generated in response to the radiation to be generated in the junction region.

Moreover, although the rotation only scanner described with reference to FIG. 1 does not have facilities for scanning the electron beam of tube 6 over the target thereof to scan the radiation in the plane of the fan 8, it will be appreciated that a tube of beam deflection kind could be used if desired. Such arrangements are described for example in U.S. Pat. No. 4,010,370.

What we claim is:

1. In a rotation only scanner for computerized axial tomography, an arrangement for detecting ionizing radiation simultaneously emergent from a body along a plurality of substantially co-planar beam paths, said arrangement comprising a detector element for each of said paths, each element including a semi-conductive device having a $p$-$n$ junction region operated in the photovoltaic current mode.

2. An arrangement according to claim 1 wherein each of said detector elements includes a scintillator device exposed to said ionizing radiation and adapted to produce, in response to the receipt thereby of said ionizing radiation, output radiation, substantially lying within the visible range of wavelengths which impinges upon the respective semi-conductive device.

3. An arrangement according to claim 2 wherein said output radiation is visible and said semi-conductive devices comprise photo-diodes.

4. An arrangement according to claim 2 wherein said scintillator devices comprise thallium activated caesium iodide crystals.

5. An arrangement according to claim 2 wherein said *p-n* junction regions are so disposed in their respective semi-conductive devices that said output radiation is substantially absorbed in the vicinity of said junction regions.

6. An arrangement according to claim 1 wherein said ionizing radiation is directly incident upon said semi-conductive devices.

7. An arrangement according to claim 6 wherein said *p-n* junction regions are so disposed in their respective semi-conductive devices that said ionizing radiation is substantially absorbed in the vicinity of said junction region.

8. An arrangement according to claim 7 wherein each of said junction regions is disposed along the respective beam path.

9. An arrangement according to claim 1 including a source of said ionizing radiation arranged to project said ionising radiation through said body along said beam paths and scanning means for scanning said source relative to said body to project radiation therethrough along further beam paths.

10. An arrangement according to claim 9 wherein said scanning means is arranged to scan said detector elements relative to said body to detect the radiation emergent therefrom along said further beam paths.

11. Radiographic apparatus including means defining a patient position, a source of ionizing radiation, such as X-radiation, arranged to project said radiation through said position along a group of divergent and substantially co-planar beam paths, scanning means for scanning said source relative to said position along further groups of beam paths substantially co-planar with said first-mentioned group, detector means for detecting the radiation emergent from the body along each of said beam paths, said detector means comprising a plurality of detector elements and containing at least a sufficient number of said elements such that one element is provided for each path of a group; each element including a semi-conductive device having a *p-n* junction operated in the photovoltaic current mode.

* * * * *